US011045398B2

(12) United States Patent
Chen et al.

(10) Patent No.: US 11,045,398 B2
(45) Date of Patent: Jun. 29, 2021

(54) SKIN-BRIGHTENING COMPOSITIONS AND METHODS

(71) Applicant: L'OREAL, Paris (FR)

(72) Inventors: Rebecca Chen, Princeton, NJ (US); Anne-Laure Suzanne Bernard, New York, NY (US); Mickael Ange Agach, Saint-Ouen (FR); Leila Safia Camille Hercouet, Neuilly Plaisance (FR); Etienne Huguet, Antony (FR)

(73) Assignee: L'OREAL, Paris (FR)

( * ) Notice: Subject to any disclaimer, the term of this patent is extended or adjusted under 35 U.S.C. 154(b) by 60 days.

(21) Appl. No.: 15/855,108

(22) Filed: Dec. 27, 2017

(65) Prior Publication Data
US 2019/0192393 A1 Jun. 27, 2019

(51) Int. Cl.
A61K 8/22 (2006.01)
A61K 8/25 (2006.01)
A61K 8/43 (2006.01)
A61K 8/31 (2006.01)
A61Q 19/00 (2006.01)
A61K 8/92 (2006.01)
A61K 8/42 (2006.01)
A61K 8/36 (2006.01)
A61K 8/37 (2006.01)
A61Q 19/02 (2006.01)
A61K 8/89 (2006.01)
A61K 8/34 (2006.01)

(52) U.S. Cl.
CPC ............... A61K 8/22 (2013.01); A61K 8/25 (2013.01); A61K 8/31 (2013.01); A61K 8/342 (2013.01); A61K 8/361 (2013.01); A61K 8/37 (2013.01); A61K 8/375 (2013.01); A61K 8/42 (2013.01); A61K 8/43 (2013.01); A61K 8/89 (2013.01); A61K 8/92 (2013.01); A61K 8/922 (2013.01); A61K 8/925 (2013.01); A61Q 19/00 (2013.01); A61Q 19/02 (2013.01); A61K 2800/30 (2013.01); A61K 2800/524 (2013.01); A61K 2800/88 (2013.01)

(58) Field of Classification Search
CPC ... A61K 8/22; A61K 8/25; A61K 8/31; A61K 8/342; A61K 8/43; A61K 8/37; A61K 8/92; A61K 8/361; A61K 8/375; A61K 8/42; A61K 8/922; A61K 8/89; A61K 8/891; A61K 8/925; A61Q 19/00; A61Q 19/02
See application file for complete search history.

(56) References Cited

U.S. PATENT DOCUMENTS

| | | | |
|---|---|---|---|
| 7,740,663 B2 | 6/2010 | De La Mettrie et al. | |
| 7,927,381 B2 | 4/2011 | Hercouet | |
| 8,556,992 B2 | 10/2013 | DeGeorge et al. | |
| 9,050,253 B2 * | 6/2015 | Tamarkin | A61L 9/122 |
| 2006/0117494 A1 | 6/2006 | Marsh | |
| 2006/0121100 A1 | 6/2006 | Opremcak | |
| 2006/0161121 A1 * | 7/2006 | Klaveness | A61K 8/22 |
| | | | 604/289 |
| 2007/0166339 A1 | 7/2007 | Gupta | |
| 2007/0186357 A1 | 8/2007 | Chalmers et al. | |
| 2008/0193393 A1 * | 8/2008 | Dayan | A61K 8/361 |
| | | | 424/59 |
| 2010/0166688 A1 | 7/2010 | Hercouet et al. | |
| 2010/0281627 A1 | 11/2010 | Matsunaga et al. | |
| 2013/0022565 A1 | 1/2013 | Braida-ValeRio et al. | |
| 2014/0341826 A1 * | 11/2014 | Nodari | A61K 8/24 |
| | | | 424/62 |
| 2016/0158123 A1 | 6/2016 | Agarwal et al. | |

FOREIGN PATENT DOCUMENTS

| | | |
|---|---|---|
| EP | 0193471 A1 | 9/1986 |
| EP | 1407751 A1 | 4/2004 |
| WO | 199960993 A1 | 12/1999 |
| WO | 2004069220 A1 | 8/2004 |
| WO | 2010070243 A1 | 6/2010 |

OTHER PUBLICATIONS

U.S. Appl. No. 15/827,726, filed Nov. 30, 2017, Chen, Rebecca.
Anonymous, "After Shave Face Moisturing Cream", Mintel, http://www.gnpd.com, XP055568115.
Anonymous, "Creme Bleach", Mintel, http://www.gnpd.com, XP055567808.

* cited by examiner

Primary Examiner — Johann R Richter
Assistant Examiner — Danielle Sullivan
(74) Attorney, Agent, or Firm — McNees Wallace & Nurick LLC

(57) ABSTRACT

A cosmetic composition for brightening skin and a method for brightening skin using the cosmetic composition are provided. The cosmetic composition has a pH<7, and includes an oxidizing agent, in some embodiments comprising hydrogen peroxide, and at least one fatty compound present from about at least 30% by weight, based upon the total weight of the composition. The method for brightening skin includes applying to the skin a composition provided as a single-part system, the system including the oxidizing agent and a fatty compound component.

27 Claims, No Drawings

SKIN-BRIGHTENING COMPOSITIONS AND METHODS

FIELD OF THE INVENTION

The present invention is generally directed to a cosmetic composition for brightening skin and a method for brightening skin using the cosmetic composition. More particularly, the present invention is directed to a cosmetic composition for brightening skin comprising an oxidizing agent, in some embodiments comprising hydrogen peroxide, and at least one fatty compound present from about at least 30% by weight, based upon the total weight of the composition, and a method for brightening skin using the cosmetic composition. The composition is characterized as having a pH<7.

BACKGROUND OF THE INVENTION

A variety of skin compositions are known that can provide skin brightening benefits. Typically, such products employ two parts i) a first part containing one or more oxidizing agents; ii) a second part containing one or more alkaline agents to activate the oxidizing agents upon mixing. One of the difficulties encountered when composing skin-brightening compositions arises because the compositions include alkaline boosters and most commonly used alkaline boosters include aqueous ammonia and/or persulfate. Aqueous ammonia is believed to allow the pH of the composition to be adjusted to an alkaline pH to enable activation of the oxidizing agent and is important to the efficacy by swelling keratinous surface. Ammonia and persulfate based alkaline boosters are known to be strong smelling and generally disagreeable to most consumers both in terms of smell as well as skin sensitivity. And the volatility of the ammonia and persulfate based alkaline boosters typically requires that the amount of booster needed must take into account the amount that will be lost due to volatilization.

It is an object of the present invention to provide a skin care composition that overcomes at least one of the aforementioned drawbacks associated with products that employ alkaline boosters and provides good skin-brightening efficacy. Yet another object of the present invention is to demonstrate a progressive increase in skin-brightening efficacy when applied regularly.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The compositions and methods hereof are characterized, in various embodiments, as comprising an oxidizing agent, in some embodiments comprising hydrogen peroxide and fatty compound, wherein the composition has a pH<7, and is a one part composition that does not include an alkaline activator component, and includes fatty compounds at a range from at least about 30% by weight, to impart on the skin a smoothing effect and a lightening effect that is comparable to conventional two part compositions that include alkaline agents.

In an exemplary embodiment, a skin-brightening cosmetic composition includes an oxidizing agent, and at least one fatty compound present in an amount of about 30% or more, by weight, based on the weight of the composition. The composition demonstrates efficiency in whitening that is at least the same as with alkaline containing compositions. In some embodiments, the oxidizing agent is selected from hydrogen peroxide, urea peroxide, carbamide peroxide, and PVP hydrogen peroxide (a complex of polyvinylpyrrolidone and hydrogen peroxide), and combinations of these.

In some particular embodiments, a skin-brightening cosmetic composition includes an oxidizing agent from about 1 to about 4 wt %, wherein in some embodiments the oxidizing agent is hydrogen peroxide, and from about 30 to about 60 wt % of at least one fatty compound. In some embodiments, the fatty compound is selected from C6-C16 lower alkanes, non-silicone oils of animal, plant, mineral or synthetic origin alcohols, fatty acids, fatty acid esters and/or fatty alcohol esters, non-silicone waxes, silicones, and combinations thereof. In some exemplary embodiments, the fatty compound includes one or more of hemisqualane, dimethicone, squalane and combinations thereof. The composition is provided as a single-part system. The composition demonstrates efficiency in whitening that is at least the same as with alkaline containing compositions.

In another exemplary embodiment, a skin-brightening cosmetic composition includes an oxidizing agent, in some embodiments comprising hydrogen peroxide, and at least one fatty compound present in an amount of about 30% or more, by weight, based on the weight of the composition, and one or more of surfactants, polymers, chelating agents and vitamins. In some particular embodiments, the at least one surfactant is present in an amount from about 0.5 to about 4%. In some embodiments, the surfactant is selected from nonionic and anionic surfactants and combinations thereof. In some embodiments, the composition includes at least one nonionic surfactant. In some embodiments, the composition includes two or more surfactants, and in some such embodiments, at least one surfactant has a low HLB (about 5) and at least one surfactant has a high HLB (about 15). The composition demonstrates efficiency in whitening that is at least the same as with ammonia containing compositions.

In another exemplary embodiment, an article of manufacture includes a packaged composition that comprises an oxidizing agent and at least one fatty compound present from about at least about 30% by weight, based upon the total weight of the composition, wherein the skin-brightening cosmetic composition has a pH<7, wherein the skin brightening composition further comprises one or more of the fatty compound and any one or more of solvents, surfactants, polymers, actives and other components.

In another exemplary embodiment, a method for brightening skin includes applying to the skin a composition comprising an oxidizing agent and at least one fatty compound present in an amount of about 30% or more, by weight, based on the weight of the composition. In some examples, the oil phase includes a combination of two or more oils. In some examples, the combinations of oils is present with each of the oxidizing components and with the alkaline booster components, and in some embodiments the oils mixed with the oxidizing and alkaline booster components may be the same or may be different, and in some examples, the percentage of oil mixed with the oxidizing and alkaline booster components may be the same or may be different. In some embodiments, the total oil content is about 50% or more. In one example, the oil is 20% mineral oil, and 40% dimethicone.

In accordance with the various embodiments, the composition provides a measurable brightening effect to keratinous tissue. In some examples, the composition when applied repeatedly over time to keratinous tissue affects a change in skin brightness (luminosity) and skin radiance.

In accordance with some of the various embodiments, the fatty compound is an oxidation resistant fatty compound.

In accordance with the various embodiments, the composition provides a measurable radiance and glow effect to keratinous tissue, whereby, when applied repeatedly over time to keratinous tissue the composition affects a change in skin radiance and glow characterized by increase in lighting of ΔL=about 1.17 without oil, ΔL=about 2.17 with about 50% oil after one application in vitro on isolated stratum corneum. This compares well to the performance of a composition that includes an alkaline booster with 55% oil, where the ΔL=about 2.18 after one application in the same in vitro test on isolated stratum corneum.

Other features and advantages of the present invention will be apparent from the following more detailed description, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

As described herein, a one part composition that is free of an alkaline activator component means that the composition does not include use of a component such as ammonia or persulfate components for purposes of activating the oxidizing agent and comprises less than a trace amount, for example, less than 0.001% by weight of the composition, of an alkaline agent, and more particularly that the agent has not been intentionally added, but may be included as a by-product or carry-over of another ingredient. In some embodiments, alkaline-free means that the composition is devoid, respectively, of alkaline agents, alkaline containing agents, and alkaline precursors thereof.

The term "alkaline agent" as used herein means compositions or ingredients comprising at least one alkaline component with a pH >7, or a pH >8. The alkaline agent may be organic or mineral or hybrid with a pKa at 25° C. greater than 7.5.

The term "oxidation resistant" means and refers to a fatty compound, such as an oil, that is free of unsaturated functions, ester groups. The fatty compound can be chosen from C6-C16 lower alkanes, non-silicone oils of animal, plant, mineral or synthetic origin fatty alcohols, fatty acids, non-silicone waxes, and silicones.

"Cosmetically acceptable" means compatible with any keratinous substrate. For example, "cosmetically acceptable carrier" means a carrier that is compatible with any keratinous substrate.

"Skin-brightening" means and refers to improvement in radiance, glow effect and lightening effect to keratinous tissue.

According to the disclosure, an acidic composition is provided, the composition having a pH<7, and in some embodiments, a pH<5, the composition including an oxidizing agent, for example, hydrogen peroxide, and at least one non-oxidizing fatty compound that is present in an amount that is greater than or equal to about 30% by weight, based on the weight of the composition. As shown herein, the composition surprisingly demonstrates skin-brightening efficacy that is comparable to two-part compositions that employ alkaline agents for activating the oxidizing agent, without the strong, unpleasant odor and high pH associated with such two-part compositions, and provides a skin smoothing effect and a glow to the skin. The brightening efficacy of the inventive composition is in some embodiments about equivalent to the brightening efficacy of two-part compositions that include alkaline agents. In some embodiments, the skin brightening efficacy of the inventive composition increases with the number of applications. Although the composition is acidic, a person skilled in the art will appreciate that the composition may include alkaline agents having a pH>7 or pH>8 such as, but not limited to, arginine, to provide functions including, but not limited to, collagen stimulation, skin healing, skin repair, skin hydration or combinations thereof.

In some embodiments, a skin-brightening cosmetic composition comprises an oxidizing agent, in some embodiments comprising hydrogen peroxide, and at least one fatty compound. The skin-brightening cosmetic composition has a pH<7. The composition demonstrates efficiency in whitening that is at least the same as with activated two-part compositions (for example those containing a first part that includes an oxidizing agent such as hydrogen peroxide and a second part that includes an alkaline booster) in which the final pH is >7.

In some embodiments, a skin-brightening cosmetic composition comprises from about 1 to about 4 wt % of an oxidizing agent, in some embodiments comprising hydrogen peroxide, and from about 30 to about 60 wt % of at least one fatty compound selected from C6-C16 lower alkanes, non-silicone oils of animal, plant, mineral or synthetic origin alcohols, fatty acids, fatty acid esters and/or fatty alcohol esters, non-silicone waxes, silicones, and combinations thereof. In some exemplary embodiments, the fatty compound includes one or more of hemisqualane, dimethicone, squalane and combinations thereof. The skin-brightening cosmetic composition has a pH<7. The composition demonstrates efficiency in whitening that is at least the same as with alkaline containing compositions.

Oxidizing Agent

The oxidizing agent in the cosmetic composition, according to the disclosure in some embodiments, is discovered to be compatible with cosmetic applications. In some embodiments, the composition may comprise one or more of hydrogen peroxide, urea peroxide, carbamide peroxide, and PVP hydrogen peroxide (a complex of polyvinylpyrrolidone and hydrogen peroxide).

In accordance with the various embodiments, amount of oxidizing agent present in the composition can range from about 1% to about 10%, from about 1 to about 7%, from about 1.0 to about 5%, from about 1.0 to about 4.0%, from 1.5 to about 3.5%, from 2.0 to about 3.0% or any suitable combination, sub-combination, range, or sub-range thereof by weight, based on the weight of the composition. One of ordinary skill in the art, however, will appreciate that other ranges are within the scope of the invention. In some embodiments, the oxidizing agent is hydrogen peroxide.

Thus, at least one oxidizing agent may be present, by weight, based on the total weight of the composition, each present from about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, to about 10 weight percent, including increments and ranges therein and there between.

Fatty Compound

In accordance with the disclosure, one or more fatty compound or oil is present in the composition. The fatty compound includes one or more of non-silicone oils of animal, plant, mineral or synthetic origin, silicone oils, hydrocarbon compounds, fatty alcohols, fatty acids, esters of a fatty acid and/or of a fatty alcohol, non-silicone waxes, and silicones.

In some embodiments, the fatty compound includes, but is not limited to: 1) 06-C16 lower alkanes, non-silicone oils of animal, plant, mineral or synthetic origin, fatty alcohols, fatty acids, non-silicone waxes, and silicones; 2) hydrocarbon-based oils of animal origin, such as perhydrosqualene (also known as "squalene"); 3) fluoro oils, perfluoromethycyclopentane and perfluoro-1,3-dimethylcyclohexane, sold under the name FLUTEC® PC1 and FLUTEC® PC3 by the company BNFL Fluorochemicals; perfluoro-1,2-dimethyl-cyclobutane; perfluoroalkanes such as dodecafluoropentane and tetradecafluorohexane, sold under the names PF 5050® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the same PF 5052® by the company 3M. 4) linear or branched saturated fatty alcohols having from 6 to 30 carbon atoms or from 8 to 30 carbon atoms, for instance cetyl alcohol, stearyl alcohol, and the mixture thereof (cetylstearyl alcohol), octyldodecanol, 2-butyloctanol, 2-hexyldecanol, 2-undecylpentadecanol, oleyl alcohol, and linoleyl alcohol.

In some embodiments, the at least one fatty compound is an organic compound that is insoluble in water at ordinary ambient temperature (25° C.) and at atmospheric pressure (760 mmHg). In some embodiments, the at least one fatty substance has a water solubility of less than 5%. In some embodiments, the at least one fatty compound has a water solubility of less than 1%. In some embodiments, the at least one fatty substance has a water solubility of less than 0.1%. Although these fatty compounds are given as an example, it will be appreciated that other compounds compatible with cosmetic applications known in the art may be used.

In some embodiments, a skin-brightening cosmetic composition comprises at least one fatty compound selected from C6-C16 lower alkanes, non-silicone oils of animal, plant, mineral or synthetic origin alcohols, fatty acids, fatty acid esters and/or fatty alcohol esters, non-silicone waxes, silicones, and combinations thereof. In some embodiments, the at least one fatty compound includes mineral oil, squalene, liquid petroleum jelly, polydecenes, silicone oil, liquid esters of fatty acids and/or of fatty alcohols, or combinations thereof. In some particular embodiments, the fatty compound includes one or more of hemisqualane, dimethicone, squalene and combinations thereof.

In accordance with the various embodiments, amounts of the fatty compounds present in the composition can range from about 30% to about 80%, or from about 35 to about 60%, from about 40 to about 59%, from about 45 to about 58%, from about 50 to about 57%, from about 52 to about 56%, from about 30 to about 55%, from about 30 to about 60% or any suitable combination, sub-combination, range, or sub-range thereof by weight, based on the weight of the composition. In some embodiments according to the disclosure, the composition includes at least about 30% of the fatty compound. And, in some embodiments according to the disclosure, the composition includes at least about 50% of the fatty compound. Thus, in some embodiments, the fatty compound is present in an amount that is not less than about 30%, or about 50%, based upon the total weight of the composition. One of ordinary skill in the art, however, will appreciate that other ranges are within the scope of the invention. In some embodiments, two or more fatty compounds are present. And, in some embodiments, one or more fatty compounds are present wherein at least one is an oxidation resistant fatty compound.

Thus, any one of or a combination of fatty compounds may be present, by weight, based on the total weight of the composition, each one or the combination present from about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, to about 80 weight percent, including increments and ranges therein and there between.

Solvent

In accordance with the disclosure, one or more solvent is present in the composition. The solvent present in the cosmetic composition, according to the disclosure, includes, but is not limited to, water, alcohol, propylene glycol, or combinations thereof. Although these solvents are given as an example, it will be appreciated that other solvents compatible with cosmetic applications known in the art may be used.

In accordance with the various embodiments, solvent is present in a given composition in an amount of from about 1% to about 70%, or any suitable combination, sub-combination, range, or sub-range thereof by weight, based on the weight of the composition. One of ordinary skill in the art, however, will appreciate that other ranges are within the scope of the invention.

Thus, one or a combination of solvents may be present, by weight, based on the total weight of the composition, each one or the combination present from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Water

The compositions comprise from about 1 to about 70% by weight of water, with respect to the total weight of the composition. In some embodiments, the amount of water in the composition can range from about 1 to about 50%, or any suitable combination, sub-combination, range, or sub-range thereof by weight, based on the weight of the composition.

The pH of the composition is not limited but is generally between 2 and 12, and in some embodiments is one of between 3 and 11, and between 5 and 9, and between 6 and 8, and 7. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Thus, water may be present by weight, based on the total weight of the composition, from about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, to about 70 weight percent, including increments and ranges therein and there between.

Surfactant

In some embodiments, the composition includes at least one surfactant. The at least one surfactant may be selected from nonionic surfactants and anionic surfactants. In some embodiments, the composition includes one, two, three or more surfactants. In some exemplary embodiments, the surfactant or surfactants are nonionic. In some embodiments, the at least one surfactant includes monoxyalkylenated or polyoxyalkylenated nonionic surfactants, monoglycerolated or polyglycerolated nonionic surfactants, alkylpolyglucoside nonionic surfactants, or combinations thereof. In some embodiments, the composition includes at least one nonionic surfactant. In some embodiments, the composition includes two or more surfactants, and in some such embodiments, at least one surfactant has a low HLB (about 5) and at least one surfactant has a high HLB (about 15).

Exemplary anionic surfactants include, but are not limited to, the salts (in particular alkali metal salts, for example, sodium salts, amine salts such as aminoalcohol salts or alkaline-earth metal salts such as magnesium salts) of the following compounds: alkyl sulfates, alkyl ether sulfates, alkylamido ether sulfates, alkylaryl polyether sulfates, monoglyceride sulfates; alkylsulfonates, alkylamidesulfonates, alkylarylsulfonates, α-olefin sulfonates, paraffin sulfonates; alkyl phosphates, alkyl ether phosphates; alkylsulfosuccinates, alkyl ether sulfosuccinates, alkylamidesulfosuccinates; alkylsulfosuccinamates; alkylsulfoacetates; acylsarcosinates; acylisethionates and N-acyltaurates; salts of fatty acids such as oleic acid, ricinoleic acid, palmitic acid or stearic acid, coconut oil acid or hydrogenated coconut oil acid; alkyl-D-galactoside uronic acid salts; acyllactylates; salts of polyoxyalkylenated alkyl ether carboxylic acids, of polyoxyalkylenated alkylaryl ether carboxylic acids or of polyoxyalkylenated alkylamido ether carboxylic acids, in particular those having from 2 to 50 ethylene oxide groups; and combinations thereof.

Exemplary nonionic surfactants include, but are not limited to, monooxyalkylenated or polyoxyalkylenated nonionic surfactants, monoglycerolated or polyglycerolated nonionic surfactants, or alkylpolyglucosides. The oxyalkylene units may be oxyethylene or oxypropylene units, or a combination thereof. In some embodiments, the oxyalkylene units are oxyethylene units. Exemplary oxyalkylenated nonionic surfactants include, but are not limited to: oxyalkylenated (C8-C24)alkylphenols, saturated or unsaturated, linear or branched, oxyalkylenated C8-C30 alcohols, saturated or unsaturated, linear or branched, oxyalkylenated C8-C30 amides, esters of saturated or unsaturated, linear or branched, C8-C30 acids and of polyethylene glycols, polyoxyethylenated esters of saturated or unsaturated, linear or branched, C8-C30 acids and of sorbitol, saturated or unsaturated, oxyethylenated plant oils, condensates of ethylene oxide and/or of propylene oxide, inter alia, alone or as a mixture.

Exemplary alkylpolyglucosides include, but are not limited to, decyl glucoside, caprylyl/capryl glucoside, laurylglucoside, coco-glucoside, cetostearyl glucoside possibly mixed with cetostearyl alcohol, arachidyl glucoside, cocoylethylglucoside, and a mixture thereof.

In some embodiments, the at least one surfactant present in the composition is a nonionic surfactant. In some exemplary embodiments, one or more surfactants in the composition are selected from oxyalkylenated (C8-C24) alkylphenols, saturated or unsaturated, linear or branched, oxyalkylenated C8-C30 alcohols, saturated or unsaturated, linear or branched, oxyalkylenated C8-C30 amides, esters of saturated or unsaturated, linear or branched, C8-C30 acids and of polyethylene glycols, polyoxyethylenated esters of saturated or unsaturated, linear or branched, C8-C30 acids and of sorbitol, saturated or unsaturated, oxyethylenated plant oils, condensates of ethylene oxide and/or propylene oxide and combinations thereof. In some exemplary embodiments a composition according to the disclosure includes two or more of non-ionic surfactants selected from oxyethylenated C8-C30 alcohols, polyoxyethylenated linear or branched, saturated or unsaturated C8-C30 acid esters, and polyoxyethylenated sorbitol esters.

In some embodiments, the composition includes two or more surfactants, and in some such embodiments, at least one surfactant has a low HLB (about 5), and in the range from about 1-8, more preferably 3≤HLB≤8, and at least one surfactant has a high HLB (about 15) and in the range from about 8-25, more preferably 10≤HLB≤16. In accordance with such embodiments, at least one surfactant has an HLB in the range from about 1 to about 8, for example from about 1, 2, 3, 4, 5, 6, 7, or 8, and at least one surfactant has an HLB in the range from about 8 to about 25, for example, from about 8, 9, 10, 11, 12, 13, 14, 15, 16, 17, 18, 19, 20, 21, 22, 23, 24 or 25. In some exemplary embodiments, a composition includes one or more of CETETH-2 (HLB ~5) and STEARETH-2 (HLB ~5), and one or more of DECYL GLUCOSIDE (HLB ~13-15) and STEARETH-20 (HLB ~15).

In some embodiments, the at least one surfactant is present in the composition in an amount ranging from about 0.1% to about 15% by weight relative to the weight of the composition. In some embodiments, the at least one surfactant is present in the composition in an amount ranging from about 0.5% to about 3.5% by weight, including increments and ranges therein and there between, based upon the total weight of the composition.

In some embodiments, one or more surfactants, alone or in combination, can be present in the composition according to the disclosure, and in some embodiments, each surfactant may be present from about 0.1% to about 5% by weight, from about 0.25% to about 2.5% by weight, from about 0.5% to about 1.8%, from about 0.5 to about 1.25%, and from about 0.5 to about 0.8%, or any suitable combination, sub-combination, range, or sub-range thereof by weight, based on the weight of the composition.

Thus, one or a combination of surfactants may be present, by weight, based on the total weight of the composition, each one or the combination present from about 0.1, 0.2, 0.3, 0.4, 0.5, 0.6, 0.7, 0.8, 0.9, 1.0, 2, 3, 4, 5, 6, 7, 8, 9, 10, 11, 12, 13, 14, to about 15 weight percent, including increments and ranges therein and there between.

Polymer

In some embodiments, one or more other components, such as polymers can be present in the composition according to the disclosure from about 0.05% to about 50% by weight, from about 0.05% to about 15% by weight, from about 0.1 to about 2%, from about 0.25 to about 1.5%, and from about 0.25 to about 0.5%, or any suitable combination, sub-combination, range, or sub-range thereof by weight, based on the weight of the composition. In some embodiments, polymers are selected from fatty acid amides, cellulose-based thickeners, guar gum and derivatives, gum of microbial origin, crosslinked homopolymers of acrylic acid or of acrylamidopropanesulfonic acid and associative polymers. In some exemplary embodiments, polymers are selected from cetyl hydroxyethylcellulose, sclerotium gum at 1% or more by weight, and combinations of these.

Thus, one or a combination of polymers may be present, by weight, based on the total weight of the composition, each one or the combination present from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Chelating Agents

In some embodiments, one or more other components, such as chelating agents can be present in the composition according to the disclosure from about 0.01% to about 2% by weight, from about 0.02% to about 1.5% by weight, from about 0.02% to about 1%, from about 0.02% to about 0.5%, and from about 0.025 to about 0.15%, or any suitable combination, sub-combination, range, or sub-range thereof by weight, based on the weight of the composition. In some exemplary embodiments, chelating agents are selected from ethylenediaminetetraacetic acid (EDTA), tetrasodium etidronate, tetrasodium pyrophosphate, pentasodium ethylenediamine tetramethylene phosphonate, sodium staminate and combinations of these.

Thus, one or a combination of chelating agents may be present, by weight, based on the total weight, each one or the combination present from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0 up to about 2 weight percent, including increments and ranges therein and there between.

Optional Components

In some embodiments, there may be one or more actives present in the cosmetic composition, according to the disclosure, the additive selected from, for example, humectants, such as acetamide MEA, glycols, such as glycerin and propylene glycol; alcohol; anti-microbial components, salicylic acid, alpha acid; antioxidants, including, but not limited to, phenolic compounds, such as chalcones, flavones, flavanones, flavanols, flavonols, dihydroflavonols, isoflavonoids, neoflavonoids, catechins, anthocyanidins, tannins, lignans, aurones, stilbenoids, curcuminoids, alkylphenols, betacyanins, capsacinoids, hydroxybenzoketones, methoxyphenols, naphthoquinones, and phenolic terpenes, resveratrol, curcumin, pinoresinol, ferulic acid, hydroxytyrosol, cinnamic acid, caffeic acid, p-coumaric acid, baicalin (Scutellaria Baicalensis root extract), pine bark extract (Pinus Pinaster bark/bud extract), ellagic acid; and vitamins and vitamin derivatives, such as tocopherol and ascorbic acid; and combinations thereof.

In some embodiments, there may be one or more other components present in the cosmetic composition, according to the disclosure, the other components selected from, fillers such as clays, talc, organic thickeners with for instance, anionic, cationic, nonionic, and amphoteric polymeric associative thickeners and combinations thereof; penetrants; sequestrants; fragrances; dispersants; film-forming agents; ceramides; opacifiers and combinations thereof. Although the aforementioned optional components are given as an example, it will be appreciated that other optional components compatible with cosmetic applications known in the art may be used.

In accordance with the various embodiments, the amount of actives and other components present in the composition can range from about 0 to about 50%, from about 0.5 to about 30%, from about 1.5 to about 20%, and from about 5 to about 15%, or any suitable combination, sub-combination, range, or sub-range thereof by weight, based on the weight of the composition.

In some embodiments, one or more actives, alone or in combination, can be present in the composition according to the disclosure from about 0.05 to about 50% by weight, from about 0.05% to about 2.5% by weight, from about 0.1 to about 2%, from about 0.25 to about 1.5%, and from about 0.5 to about 1.25%, or any suitable combination, sub-combination, range, or sub-range thereof by weight, based on the weight of the composition.

In some embodiments, one or more other components, such as preservatives, vitamins, preservatives, and the like, alone or in combination, can be present in the composition according to the disclosure from about 0.05 to about 50% by weight, from about 0.05% to about 25% by weight, from about 0.1 to about 10%, from about 0.25% to about 5%, and from about 0.5 to about 3.5%, or any suitable combination, sub-combination, range, or sub-range thereof by weight, based on the weight of the composition. In some exemplary embodiments, preservatives may include sodium salicylate, and vitamins may include ascorbic acid, tocopherol and combinations of these.

Thus, one or a combination of optional components may be present, by weight, based on the total weight of the composition, each one or the combination present from about 0.05, 0.06, 0.07, 0.08, 0.09, 0.1, 0.2, 0.3, 0.4, 0.5, 0.6, 0.7, 0.8, 0.9, 1.0, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 weight percent, including increments and ranges therein and there between.

Articles of Manufacture

In accordance with the various embodiments, the composition may be provided in a kit or other article of manufacture, such as, a mask, cream, or lotion, wherein the kit may include packaging of the composition in one or more packages or containers. In some embodiments, the one or more packages or containers may be selected from packet chambers and tubes.

In one example, the article of manufacture may be a packet with a single chamber. In some other embodiments, the packaging is a single tube. In other embodiments, the packaging can be a single container holding a suspension of encapsulated material. In other embodiments, the article of manufacture may include more than one package, wherein each one of any one or more of the sub composition comprising at least one oil and any one or more of solvents, surfactants, polymers, actives and other components of the composition is separately packaged from the sub composition comprising at least one oxidizing agent.

In accordance with the various embodiments, a skin-brightening cosmetic composition is in a form including a suspension, lotion, cream, serum, essence, gel, stick, spray, ointment, paste, foam, mousse, cream, wipe, patch, strip, film-forming product, facial masks or skin masks.

EXAMPLES

Inventive Compositions

TABLE 1

| | Inventive Example 1 | Inventive Example 2 | Inventive Example 3 | Inventive Example 4 |
|---|---|---|---|---|
| Chelating agents | 0.15 | 0.15 | 0.15 | 0.15 |
| (FATTY COMPOUND SILICONE OIL) DIMETHICONE | | | 40 | |
| (FATTY COMPOUND SQUALANE) | | 50 | | |
| C13-15 ALKANE (FATTY COMPOUND) MINERAL OIL | 50 | | 10 | 30 |
| HYDROGEN PEROXIDE | 3.5 | 3.5 | 3.5 | 3.5 |

TABLE 1-continued

| | Inventive Example 1 | Inventive Example 2 | Inventive Example 3 | Inventive Example 4 |
|---|---|---|---|---|
| PRESERVATIVE | 0.035 | | 0.035 | 0.035 |
| NONIONIC SURFACTANTS (INCLUDING LOW AND HIGH HLB) | 3.5 | 3.5 | 3.5 | 3.5 |
| (VITAMIN) | 0.2 | 0.2 | 0.2 | 0.2 |
| (SOLVENT) WATER | QS 100 | QS 100 | QS 100 | QS 100 |

Comparative Compositions

Table 2 A and 2B: Comparative cosmetic compositions

TABLE 2A

| | Comparative Example 1 | | |
|---|---|---|---|
| Type | PART A | PART B | FINAL (A + B, EQUAL PARTS) |
| BOOSTER (GUANIDINE CARBONATE) | 0 | 4 | 2 |
| HYDROGEN PEROXIDE | 7 | 0 | 3.5 |
| FATTY COMPOUND | 50 | 60 | 55 |
| NONIONIC SURFACTANTS | 3.5 | 3.5 | 3.5 |
| CHELATING AGENTS | 0.15 | 0.15 | 0.15 |
| VITAMINS | 0.2 | 0.2 | 0.2 |
| POLYMER | 0.75 | 0.75 | 0.75 |
| PRESERVATIVE | 0.02 | 0.02 | 0.02 |
| WATER | QS 100 | QS 100 | QS 100 |

TABLE 2B

| | Comparative Example 2 |
|---|---|
| CHELATING AGENTS | 0.15 |
| HYDROGEN PEROXIDE | 3.5 |
| NONIONIC SURFACTANTS | 3.5 |
| VITAMINS | 0.2 |
| POLYMER | 0.75 |
| PRESERVATIVE | 0.02 |
| WATER | QS 100 |

In Vitro Stratum Corneum Testing:

In vitro stratum corneum tests were conducted as follows: three stratum corneum samples (pre-conditioned for 17 h at 75% relative humidity) were treated with compositions for an exposure period of 15 minutes with no external heat or occlusion. Following treatment, the samples were rinsed and dried. The color of the stratum corneum was measured before and after treatment, and the individual change of Luminosity L* before and after treatment on white background was calculated and reported as ΔL (change in luminosity).

In Vivo Skin Testing:

In vivo clinical studies were conducted among dark skin tone population. Tested compositions were applied on half of the face, and were left on for 15 min and then rinsed off and air dried. Skin Brightness and radiance were evaluated by clinical scoring. Applications of compositions were made once per week and evaluation was made two hours after treatment. Skin brightness and radiance was evaluated by clinical scoring, which uses experts to rate the skin brightness and radiance based on rating scales. Skin radiance is a subjective concept based on people perception, usually relates to a combination of even tone (color), luminosity (contrast), imperfections (dark circles, spots) and firmness. The skin radiance level is evaluated by experts based on a 1-5 scale of clinical scoring wherein the radiance score ranges from =dull, least radiant or bright to 5=most radiant or bright.

Results:

Example 1: Efficacy Increases with Increased Oil Content

Inventive composition is the Inventive Example 1 shown in Table 1; Comparative compositions are shown in Tables 2A and 2B. The inventive composition is a one-part without alkaline activation and has a final pH<7, and the comparative is a two-part composition that is activated with an alkaline agent and has a final pH>7.

Table 3 Lightening of skin using compositions having a pH>7 and pH<7 were assessed in vitro, wherein the ΔL as reported is based on an average of three data points.

TABLE 3

| Type | Water | Comparative Example 1 (With alkaline booster, pH > 7) | Comparative Example 2 (No alkaline booster; No oil, pH > 7) | Inventive Example 1 (50% oil, pH < 7) | Inventive Example 2 (30% oil, pH < 7) |
|---|---|---|---|---|---|
| HYDROGEN PEROXIDE | 0 | 3.5% | 3.5% | 3.5% | 3.5% |
| GUANADINE BICARBONATE | 0 | 2% | 0 | 0 | 0 |
| OIL | 0 | 55% | 0% | 50% | 30% |
| ΔL on SC with white background | 0.65 ± 0.17 | 2.18 ± 0.28 | 1.17 ± 0.3 | 2.17 ± 0.27 | 2.24 ± 0.48 |

Both inventive (pH<7, non-activated) and comparative (pH>7, activated) compositions provide comparable stratum corneum lightening efficacy. The brightening efficacy of the inventive composition increases as the oil content increases from between about 0% to about 50%, including at 30%. The lightening efficacy with the inventive compositions including oil were significantly better than those without oil, and the results were comparable between the compositions with oil+11 alkaline booster. As shown in Table 4, below, the lightening improved with repeated applications over time.

Example 2: Efficacy Increases with Repeated Application

Inventive composition is the Inventive Example 1 shown in Table 1; Comparative composition is shown in Table 2A.

Table 4 Lightening of skin increases over time in in vivo Skin Brightness and Radiance tests.

TABLE 4

| Type | Comparative Example 1 (pH > 7) | Inventive Example 2 (50% oil, pH < 7) |
|---|---|---|
| HYDROGEN PEROXIDE | 3.5% | 3.5% |
| GUANADINE BICARBONATE | 2% | 0 |
| OIL | 55% | 50% |
| Skin Brightness ΔL | D 0: 2.58 ± 0.15 | D 0: 2.58 ± 0.15 |
|  | D 3: 3.3 ± 0.15 | D 3: 3.08 ± 0.15 |
|  | D 7: 3.5 ± 0.15 | D 7: 3.38 ± 0.15 |
|  | D 14: 3.7 ± 0.15 | D 14: 3.65 ± 0.15 |
| Radiance/Glow | D 0: 2.78 ± 0.15 | D 0: 2.78 ± 0.15 |
|  | D 3: 3.2 ± 0.15 | D 3: 3.12 ± 0.15 |
|  | D 7: 3.62 ± 0.15 | D 7: 3.58 ± 0.15 |
|  | D 14: 3.9 ± 0.15 | D 14: 3.82 ± 0.15 |

The foregoing results as shown in Table 4 demonstrate in increasing brightening effect on the skin over time after at least two applications.

Raw Materials

Compositions and compositions as described in the representative embodiments herein are selected from commercially available materials, including, for example: hydrogen peroxide; mineral oil, hemisqualane, and guanidine carbonate.

The articles "a" and "an," as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A skin-brightening cosmetic composition comprising:
   a. at least one oxidizing agent comprising hydrogen peroxide, urea peroxide, carbamide peroxide, PVP hydrogen peroxide, or a combination thereof, present from about 1 to about 5% by weight, based upon the total weight of the composition;
   b. at least one nonionic surfactant; and
   c. at least one oil present from about at least 50% by weight, based upon the total weight of the composition, wherein the skin-brightening cosmetic composition is free of any alkaline agent, and
   wherein the skin-brightening cosmetic composition has a pH<7.

2. The composition of claim 1, wherein the composition is provided as a single part system.

3. The composition of claim 1, wherein the composition, when applied repeatedly over time to keratinous tissue affects a change in skin brightness.

4. The composition of claim 1, wherein the oxidizing agent is employed in an amount of from about 1 to about 4% by weight, based on the weight of the composition.

5. The composition of claim 1, wherein the oxidizing agent is hydrogen peroxide.

6. The composition of claim 1, wherein the at least one oil is employed in an amount of from about 50 to about 60% by weight, based on the weight of the composition.

7. The composition of claim 1, wherein the at least one oil is selected from the group consisting of silicone oil, mineral oil, dimethicone, squalene, squalane, hemisqualane, and combinations thereof.

8. The composition of claim 1 further comprising a polymer selected from the group consisting of fatty acid amides, cellulose-based thickeners, guar gum and derivatives, gum of microbial origin, crosslinked homopolymers of acrylic acid homopolymers of acrylamidopropanesulfonic acid and associative polymers.

9. The composition of claim 1 further comprising a preservative that comprises sodium salicylate.

10. The composition of claim 1, wherein the at least one surfactant is selected from the group consisting of monoxyalkylenated or polyoxyalkylenated nonionic surfactants, monoglycerolated or polyglycerolated nonionic surfactants, alkylpolyglucosides, and combinations thereof.

11. The composition of claim 1 further comprising a vitamin or vitamin derivative selected from the group consisting of ascorbic acid, tocopherol and combinations thereof.

12. The composition of claim 1 further comprising a solvent comprising water.

13. The composition of claim 1 that further comprising one or more of a chelating agent and a pH adjuster consisting of one or a combination of ethylenediaminetetraacetic acid (EDTA), tetrasodium etidronate, tetrasodium pyrophosphate, phosphoric acid, and citric acid.

14. The composition of claim 1 is in a form selected from the group consisting of a suspension, cream, serum, essence, gel, toner, stick, spray, ointment, paste, foam, mousse, shaving cream, wipe, patch, strip, film-forming product, facial masks and skin masks.

15. A skin-brightening cosmetic composition comprising:
   a. from about 1 to about to about 5 wt % of an oxidizing agent comprising hydrogen peroxide; and
   b. from about 50 to about 60 wt % of at least one oil selected from the group consisting of silicone oil, mineral oil, dimethicone, squalene, squalane, hemisqualane, and combinations thereof,
   wherein the skin-brightening cosmetic composition is free of any alkaline agent, and
   wherein the skin-brightening cosmetic composition has a pH<7.

16. The composition of claim 15, wherein the composition is provided as a single-part system.

17. The composition of claim 15 further comprising a polymer, a preservative, a surfactant, a vitamin, a vitamin derivative, a solvent, a chelating agent, or combinations thereof.

18. The skin-brightening cosmetic composition according to claim 15, wherein the first composition includes one or more of a chelating agent and a pH adjuster consisting of one or a combination of ethylenediaminetetraacetic acid (EDTA), tetrasodium etidronate, tetrasodium pyrophosphate, phosphoric acid, and citric acid.

19. A method for brightening skin, comprising applying to the skin a composition comprising:
   a. at least one oxidizing agent comprising hydrogen peroxide, urea peroxide, carbamide peroxide, PVP hydrogen peroxide, or a combination, and present from about 1 to about 5% by weight, based upon the total weight of the composition;
   b. at least one nonionic surfactant; and
   c. at least one oil present from about at least 50% by weight, based upon the total weight of the composition, wherein the skin-brightening cosmetic composition is free of any alkaline agent, and
   wherein the skin-brightening cosmetic composition has a pH<7, and
   wherein the composition is provided as a single-part system.

20. The method of claim 19, wherein the oxidizing agent is employed in an amount of from about 1 to about 4% by weight, based on the weight of the composition.

21. The method of claim 19, wherein the at least one oil is employed in an amount of from about 50 to about 60% by weight, based on the weight of the composition and is selected from the group consisting of silicone oil, mineral oil, dimethicone, squalene, squalane, hemisqualane, and combinations thereof.

22. The method of claim 19 further comprising a polymer, a preservative, a surfactant, a vitamin, a vitamin derivative, a solvent, a chelating agent, or combinations thereof.

23. The method for brightening skin according to claim 19, wherein the composition includes one or more of a chelating agent and a pH adjuster consisting of one or a combination of ethylenediaminetetraacetic acid (EDTA), tetrasodium etidronate, tetrasodium pyrophosphate, phosphoric acid, and citric acid.

24. An article of manufacture for providing a skin brightening composition, the skin brightening composition comprising:
   a. a first sub-composition comprising at least one oxidizing agent present from about 1 to about 5% by weight, based on the weight of the composition; and
   b. a second sub-composition comprising at least one oil present from about at least 50% by weight, based upon the total weight of the composition,
   wherein the skin-brightening cosmetic composition is free of any alkaline agent, and
   wherein the skin-brightening cosmetic composition has a pH<7, and
   wherein the skin brightening composition further comprising one or more other components selected from the group consisting of solvents, surfactants, polymers, actives and combinations thereof.

25. The article of manufacture according to claim 24, wherein any one or more of the second sub-composition comprising the at least one oil and any one or more of solvents, surfactants, polymers, actives or combinations thereof is separately packaged from the first sub composition.

26. The article of manufacture according to claim 24, wherein the first sub-composition includes one or more of a chelating agent and a pH adjuster consisting of one or a combination of ethylenediaminetetraacetic acid (EDTA), tetrasodium etidronate, tetrasodium pyrophosphate, phosphoric acid, and citric acid.

27. The article of manufacture according to claim 24, wherein each of the first and second sub-compositions are packaged in a single package.

* * * * *